United States Patent
McKinney et al.

(10) Patent No.: US 7,518,054 B2
(45) Date of Patent: Apr. 14, 2009

(54) AUDIO REPRODUCTION APPARATUS, METHOD, COMPUTER PROGRAM

(75) Inventors: Martin Franciscus McKinney, Eindhoven (NL); Dirk Jeroen Breebaart, Eindhoven (NL); Steven Leonardus Josephus Dimphina Elisabeth Van de Par, Eindhoven (NL); Ludovic Albert Jozef Van Paepegem, Leuven (BE)

(73) Assignee: Koninlkijke Philips Electronics N.V., Eindhoven (NL)

( * ) Notice: Subject to any disclaimer, the term of this patent is extended or adjusted under 35 U.S.C. 154(b) by 3 days.

(21) Appl. No.: 10/545,185

(22) PCT Filed: Jan. 28, 2004

(86) PCT No.: PCT/IB2004/050059

§ 371 (c)(1),
(2), (4) Date: Apr. 11, 2006

(87) PCT Pub. No.: WO2004/072767

PCT Pub. Date: Aug. 26, 2004

(65) Prior Publication Data
US 2007/0044641 A1 Mar. 1, 2007

(30) Foreign Application Priority Data
Feb. 12, 2003 (EP) .................... 03100307

(51) Int. Cl.
  *G10H 1/40* (2006.01)
  *G10L 21/04* (2006.01)
  *A63B 71/00* (2006.01)
  *G06F 17/00* (2006.01)

(52) U.S. Cl. ............... 84/612; 704/503; 482/9; 700/94

(58) Field of Classification Search ........... 84/465, 84/612; 482/3, 8, 9; 704/503, 504; 700/94
See application file for complete search history.

(56) References Cited

U.S. PATENT DOCUMENTS 5,215,468 A * 6/1993 Lauffer et al. ............... 434/236

(Continued)

FOREIGN PATENT DOCUMENTS

EP   1251441 A1   10/2002

(Continued)

OTHER PUBLICATIONS

Eric D. Scheir: Tempo and Best Analysis of Acoustic Musical Signals, vol. 103, Jan. 1998, pp. 588-601.

(Continued)

*Primary Examiner*—Walter Benson
*Assistant Examiner*—Andrew R Millikin (57) ABSTRACT

The audio reproduction apparatus (100) for sports training purposes comprises a tempo derivation unit (103) for deriving a selected tempo (T) on the basis of a data signal (d1, d2, d3) e.g. from a sports measurement device such as a heart rate meter; and an audio conditioning unit (104) arranged to deliver based on the input audio signal the output audio signal, with a tempo within a predefined accepted deviation from the selected tempo (T), whereby the audio conditioning unit (104) comprises a tempo calculation unit (106) arranged to calculate an input tempo (TI) of the input audio signal, and the audio conditioning unit (104) is arranged to deliver the output signal in dependence of the input tempo (TI).

20 Claims, 6 Drawing Sheets

U.S. PATENT DOCUMENTS

| | | | |
|---|---|---|---|
| 5,235,761 A | 8/1993 | Chang | |
| 5,267,942 A * | 12/1993 | Saperston | 600/28 |
| 5,629,491 A * | 5/1997 | Usa | 84/636 |
| 5,952,596 A * | 9/1999 | Kondo | 84/605 |
| 6,049,766 A * | 4/2000 | Laroche | 704/216 |
| 6,232,540 B1 * | 5/2001 | Kondo | 84/612 |
| 6,336,891 B1 | 1/2002 | Fedrigon et al. | |
| 6,835,885 B1 * | 12/2004 | Kondo et al. | 84/612 |
| 2001/0015123 A1 | 8/2001 | Nishitani et al. | |
| 2001/0035087 A1 | 11/2001 | Subotnick | |

FOREIGN PATENT DOCUMENTS

| | | |
|---|---|---|
| EP | 1251441 A2 * | 10/2002 |
| JP | 2001299980 A | 10/2001 |
| WO | 9820482 A1 | 5/1998 |
| WO | 0205124 A1 | 1/2002 |
| WO | 0237471 A2 | 5/2002 |

OTHER PUBLICATIONS

R. W. Picard, et al: Affective Wearables, IEEE 1997, pp. 90-97.
R. W. Picard, et al: Affective Wearables, IEEE 1997, pp. 90-97.

* cited by examiner

AUDIO REPRODUCTION APPARATUS, METHOD, COMPUTER PROGRAM

The invention relates to an audio reproduction apparatus suitable for use during sports training comprising:
- an input for inputting an input audio signal;
- an output for outputting an output audio signal;
- a user behavior identification unit capable of providing a data output; and
- an audio conditioning unit for conditioning the output audio signal dependent on the data output from the user behavior identification unit.

The invention further relates to a method for delivering an output audio signal with an output tempo within a predefined deviation from a selected tempo comprising:
- inputting an input audio signal;
- deriving a selected tempo on the basis of a data signal; and
- delivering based on the input audio signal an output audio signal, with an output tempo within a predefined deviation from the selected tempo.

The invention further relates to a computer program product comprising commands enabling a processor to execute the method.

A variant of such an apparatus is known from US2001/0035087-A. The apparatus contains an embodiment of a user behavior identification unit being a gesture input and interpretation module. In the known apparatus, the gesture input and interpretation module typically analyzes a trajectory of e.g. a mouse movement, the mouse being moved by a user. The known apparatus also contains an audio conditioning unit, called a playback decision module, for selecting from a music database pieces of music with a particular emotional character corresponding to the gesture made. E.g. moving the mouse up and down in an excited way may result in the selection of a piece of music containing drum sounds. One of the available emotional characters that can be used for selection mentioned in the cited document is a selected tempo of the pieces of music.

It is a disadvantage of the known apparatus that it is not flexible. Pieces of music have to be tagged in advance by a person, the tag describing the emotional character of the piece of music, which severely limits the number of available pieces of music which can be used with the known apparatus. If the gestures are used to compose a composition of music pieces, it will not sound very beautiful if there is only a limited set to choose from. Furthermore a tag typically specifies a tempo in a vague manner, such as: the tempo is "fast", "very fast", "slow" or "excited". An additional problem of the known apparatus is that each piece of music has a fixed tempo, as noted in its tag. Attempting to solve this problem, the known document describes another embodiment of the known apparatus which contains a musical instrument digital interface (MIDI) coder. A MIDI signal of a known tempo can be recoded to a new tempo. However the fact that this only applies to electronic music is again a flexibility limitation.

It is a first object of the invention to provide an apparatus of the kind mentioned in the opening paragraph which is relatively flexible as to the types of input audio signal, e.g. music, that can be used as input to deliver an output audio signal of substantially the selected tempo.

It is a second object to provide a method of the kind mentioned in the opening paragraph which is relatively flexible as to the types of input audio signal, e.g. music, that can be used as input to deliver an output audio signal of substantially the selected tempo.

The first object is realized in that
- the user behavior identification unit is a tempo derivation unit for deriving the data output being a selected tempo, on the basis of a data signal;
- the audio conditioning unit comprises a tempo calculation unit arranged to calculate an input tempo of the input audio signal; and
- the audio conditioning unit is arranged to deliver the output audio signal with an output tempo within a predefined deviation from the selected tempo, the output signal depending on the input tempo.

When analyzing user gestures, an excitedness of up and down movement of a mouse can be used for the derivation of an approximate indication of the selected tempo. However the selected tempo can be derived much more accurately on the basis of a data signal from e.g. a pace meter on a running shoe. Such tempo measuring devices allow new applications, e.g. in sports. It is known that runners tend to run with a pace corresponding to the tempo of music playing, so an apparatus providing music of the correct tempo to the runner can facilitate his training. In general, in the apparatus according to the invention, the selected tempo is selected by a person doing sports or being engaged in a similar activity, such as a soldier on a march, according to his requirements.

The tempo calculation unit is comprised as a key feature of the apparatus according to the invention, to enable the apparatus to determine the input tempo of most types of input audio signal, e.g. real music from a radio or MP3 decoded audio, electronic music, or if required even speech.

An embodiment of the audio reproduction apparatus according to the invention comprises selection means capable of selecting as the input audio signal a piece of audio from an audio source, and the audio conditioning unit is arranged to deliver the output audio signal based on the input audio signal if a condition is met, being: the absolute difference between the selected tempo and the input tempo is below the predefined deviation. The selection means are arranged to search the audio source and select from it different pieces of audio or music as the input audio signal, until a piece of audio or music is found of roughly the selected tempo. Once the condition is met, in a simple variant of the embodiment, the conditioning unit is arranged to send the input audio signal to the output as the output audio signal. Since in this case the output signal is the input signal, the absolute difference condition on the output tempo can be formulated as an absolute difference condition on the input tempo. An advantageous instance of the audio source is a memory containing MP3 encoded audio. Nowadays a typical memory, which may be included in the audio reproduction apparatus, can store hundreds of pieces of music, so a nice training composition can be constructed from them for whichever training session. Another variant of the selection means is arranged to search radio channels to find the correct music.

In an advanced variant of the embodiment, the audio conditioning unit further comprises an audio processing unit, arranged to derive, based upon the input audio signal, the output signal with an output tempo closer to the selected tempo than the input tempo. The audio processing unit may be arranged to apply a tempo adjustment-realized in software or hardware-which offers the option of finetuning or in general adjusting an incorrect tempo of a selected input audio signal from the audio source. This is interesting in case there is not much music available in the audio source with substantially the selected tempo. The audio-processing unit may also be arranged to compensate for tempo variations within a selected piece of music. A simple algorithm for changing the tempo constructs the output audio signal by adding samples of the input signal to a substantially zero output signal, at time instances determined by the selected tempo, and applying an interpolation filter. This algorithm results in a difference of pitch of the input and the output audio signal, which may for large tempo adjustments lead to a cartoon-like reproduction of singing voices, and off key music. Pitch preserving tempo-changing algorithms can be applied in a high quality variant of the advanced variant, as described below for a different embodiment.

An alternative embodiment of the audio reproduction apparatus according to the invention comprises an audio processing unit, arranged to construct, based on the input audio signal, the output audio signal with an output tempo closer to the selected tempo than the input tempo, and with an output pitch substantially equal to an input pitch of the input signal. By incorporating such an audio processing unit, it is not necessary to comprise selection means, since each input audio signal can be processed to obtain an output audio signal of roughly the selected tempo. Of course selection means may be present to select the input audio based on different criteria, e.g. by a user.

In a specific variant of the alternative embodiment, the audio conditioning unit comprises an audio processing unit, arranged to construct, based on the input audio signal, the output audio signal with an output tempo closer to the selected tempo than the input tempo, starting from a substantially zero value output audio signal, by adding input audio segments of consecutive samples of the input audio signal to the output audio signal, at output time instances determined by the ratio between the selected tempo and the input tempo, the input audio segments being selected on the basis of a predefined audio segment similarity criterion, and the samples in the segments being weighed by a predefined weighing function before being added to the output audio signal. The idea behind this algorithm is that pitch corresponds to a short time scale variation of the audio signal, whereas tempo manifests itself on a longer time scale, e.g. a quarter of a second. On the short time scale successive segments of the audio signal are relatively similar—e.g. for a particular audio signal they are similar in each $400^{th}$ of a second interval—, a fact of nature which a human ear exploits to determine the pitch. By means of the predefined audio segment similarity criterion, the similar segments in the input audio signal are extracted. They are added to the output audio signal at the required temporal positions. E.g. if the output tempo is half as fast as the input tempo, the input audio segments are placed in the output audio signal twice as far apart in time as in the input audio signal. The gaps in between are filled by copying the input audio segments to the output audio signal again, or by adding calculated segments similar to the local input audio segments. Since the neighboring segments are similar, copying more or less of these similar segments to the output audio signal hardly changes the perceptual characteristics of the output audio signal as compared to the input audio signal, apart from the tempo or duration. The weighing is included to make the output audio signal smoother, leading to a reduction in the amount of perceptible artifact.

It is advantageous if the audio processing unit comprises a local tempo variation unit, arranged to apply between a first input audio segment and a first output audio segment, based on the first input audio segment, a first tempo adjustment with a first tempo change, and to apply between a second input audio segment and a second output audio segment, based on the second input audio segment, a second tempo adjustment with a second tempo change, whereby the first tempo change is different from the second tempo change. E.g., by slowing the duration of some notes, e.g. played on a trumpet, more than the duration of notes in their the temporal environment, an additional suggestion of slowness can be simulated, which is advantageous for obtaining relaxing music.

The audio reproduction apparatus may further comprise a workout scheme specification unit, arranged to allow a specification of a series of consecutive selected tempos. This enables a user to specify an entire workout scheme, only as a set of tempos, so that the actual music played can still be varied according to his desire. The specification may be done during the exercise or at home on a p.c. and downloaded to the apparatus. Other people than the user may also contribute to the specification.

The second object is realized in that the method is characterized in that an input tempo of the input audio signal is calculated, and the output signal is delivered in dependence of the input tempo.

These and other aspects of the audio reproduction apparatus according to the invention will be apparent from and elucidated with reference to the implementations and embodiments described hereinafter, and with reference to the accompanying drawings, which serve merely as non-limiting illustrations.

In the Drawings

In these Figures elements drawn dashed are optional, depending on the desired embodiment.

Figure 1:
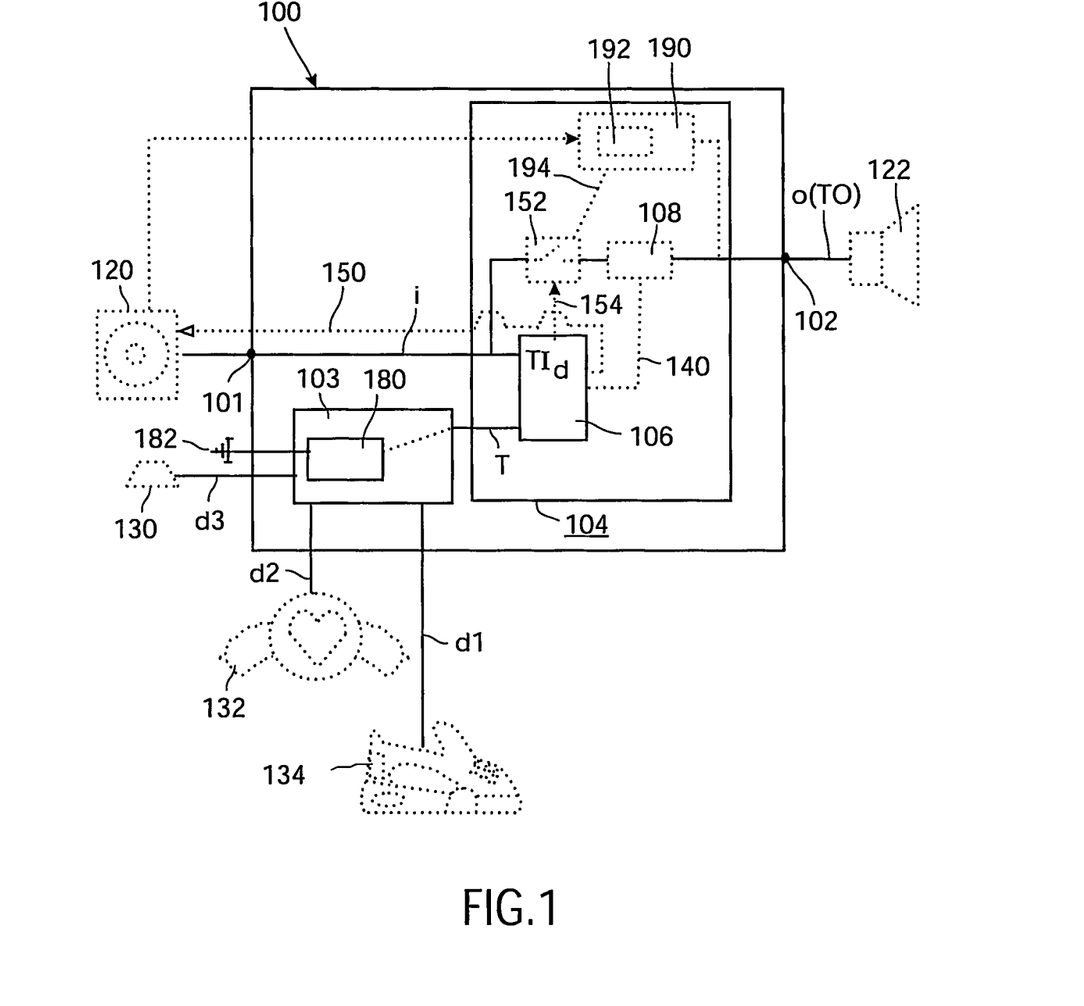
FIG. 1 schematically shows the audio reproduction apparatus according to the invention.

FIG. 1 shows an audio reproduction apparatus 100 with an input 101 for inputting an input audio signal i, and an output 102 for outputting an output audio signal o, typically derived from the input audio signal. The audio reproduction apparatus is intended for sports training or similar activity and comprises a tempo derivation unit 103 for deriving a selected tempo T on the basis of a data signal d1, d2, d3. The audio reproduction apparatus 100 may e.g. be portable, connectable to a wearable sports measurement device or may be attached to a fitness apparatus. E.g. a runner may wear a sports shoe containing a pace meter 134, which measures the runner's pace i.e. how many steps are taken each second, e.g. based on an acceleration sensor or a deformation sensor. E.g., based on an acceleration timeline the acceleration sensor may transmit a number representing the pace as a first data signal d1 to the tempo derivation unit 103. Alternatively, the tempo derivation unit 103 may be arranged to perform the computation of the pace based on an incoming first data signal d1 comprising the acceleration timeline. The tempo derivation unit 103 may be arranged to calculate a selected tempo T based on the measured runner's pace, according to a selection strategy. E.g. the selected tempo can be set equal to or within a predefined interval of the pace. The runner can then listen to music of an output tempo substantially equal to his pace, which makes his running easier. The pace can e.g. be measured at a number of time instances and an average pace can be determined as a baseline. If the runner then runs uphill for a short time, the selected tempo and hence the output tempo is not adjusted, so that the music motivates him to keep running at the same pace.

In an alternative tempo selection strategy, a desired training level can be set. E.g. a heart rate meter 132 on a step machine in a fitness center may be transmitting the heart rate of a user exercising to the tempo derivation unit 103. A desired heart rate is set on the step machine. As long as the actual heart rate of the user is below the desired heart rate, for a predefined interval of time to take into account adaptations in the heart rate of the user to increased exercise load conditions, fast music is played. The user can then fasten his step according to the output tempo of the music. The desired heart rate may come in as a second data signal d2 together with the actual heart rate of a user at a time instance, or they may be two different data signals into the tempo derivation unit 103. The user can also specify a selected tempo T by means of a user input 130 as a third data signal d3. Other measurement devices characterizing sports activities may also be used, such as e.g. an oxymeter, a breathing analyser, or the onboard computer of a training apparatus which e.g. sends as a data signal the speed of a rolling carpet.

A workout scheme specification unit 180 may also be present, which is arranged to allow a user to specify a series of consecutive selected tempo's T according to his desire, formulating an exercise schedule for successive time intervals. E.g. the user wants to start training with slow warm up music, then likes to continue with ten minutes strenuous exercise requiring music of a fast tempo, and ending with slow music for cool down and relaxation purposes. If synchronization means 182 are connected to the workout scheme specification unit 180, e.g. a wired or wireless connection to a master server or another similar audio reproduction apparatus, group training or training games in which a first user selects the selected tempo for a second user become possible. E.g. the selection means may comprise a connection to an Internet server on which a personal trainer has stored a daily training profile.

Given the selected tempo T, an audio conditioning unit 104 is arranged to deliver based on the input audio signal i the output audio signal o, with an output tempo TO within a predefined deviation d from the selected tempo T. The input audio signal i originates from an audio source of audio pieces, which may be e.g. a radio receiver, but advantageously may be a database of music pieces in the audio reproduction apparatus, such as a memory containing compressed audio files, or a CD reader. A tempo calculation unit 106 is arranged to calculate an input tempo TI of the input audio signal i. If a condition is met, being the absolute difference between the selected tempo T and the input tempo TI is below the predefined deviation d, the audio conditioning unit 104 may be configured to transmit the input signal i as the output signal o to the output 102. In a simple realization, the tempo calculation unit 106 is arranged to send a control signal over a first control connection 154 to a switch 152. If the input audio signal is of roughly the desired selected tempo the switch 152 is closed and otherwise it is open. The output 102 may be connected to a sound production means 122, such as a loudspeaker, or advantageously headphones.

If the absolute difference between the selected tempo T and the input tempo TI is above the predefined deviation d, the input audio signal does not conform to the user's likings as expressed in the selected tempo T, and some action has to be taken by the audio conditioning unit 104. Otherwise, in the simple realization the user hears no output audio as long as the condition is not met, since the switch 152 is open. The switch could be forced closed, but then music of the wrong output tempo is outputted. An embodiment of the audio reproduction apparatus 100 comprises selection means 150 which is arranged to select individual pieces audio from the audio source 120. The selection means 150 may e.g. be realized as a data connection or bus to the audio source 120, transmitting a "next song" commando or an index of a song, in case the input tempo TI is incorrect. The selection process continues until an audio piece of substantially the selected tempo is found. Instead of calculating the input tempo TI of a piece of audio on the fly, a memory 160 (see FIG. 2) may be comprised, which contains a table of indices of audio pieces from the audio database and corresponding input tempo's TI, which table may typically be enlarged each time a piece of audio is loaded as an input signal and its tempo is calculated by the tempo calculation unit 106. The advantage of such a table is that an audio piece of substantially the correct input tempo TI can immediately be selected, instead of having to go through and analyze all the audio pieces sequentially each time. The audio source 120 may comprise a set of versions of the same song or audio piece with different tempos. This is interesting for a variant of the audio reproduction apparatus 100, which is only arranged to select input audio of substantially the desired tempo and is not arranged to change the tempo of a selected piece of audio. A song may then be processed to obtain 10 versions of different tempo—e.g. on a p.c.—, which are then downloaded into the audio source 120 of e.g. a portable solid state MP3 or CD player.

While the selection means are searching for the correct song, and the condition is not met, a fallback audio setting unit 190 detecting the state of the switch 152 by means of detecting means 194, may furnish the output audio signal o, by temporarily supplying e.g. a default audio piece or the previous audio piece. The fallback audio setting unit 190 may comprise an artificial audio generator 192 arranged to temporarily create an artificial output audio signal o, such as a sequence of audio segments containing a drum beat, or a sequence of electronic beeps.

Another embodiment may additionally or alternatively comprise an audio processing unit 108, arranged to construct the output audio signal o with an output tempo TO being roughly the selected tempo T, i.e. within the deviation d of the selected tempo T, on the basis of the input signal i. Like all the functional components of the audio reproduction apparatus it may be realized as a hardware circuit or as a method running as software on a processor. A first possible way to derive an output audio signal o similar to the input audio signal i but of changed tempo, samples the input signal, places the samples in the output signal at a different intersample distance, and interpolates and/or filters. In a variant, a number of successive samples of the input audio signal is used to determine an output audio sample, e.g. by means of model prediction. Those algorithms in general introduce a perceptible change in pitch. Hence pitch-preserving tempo changing algorithms may also be employed by the audio-processing unit 108, such as the one described with the aid of FIG. 5. In order to realize the tempo adjustment, the audio processing unit 108 may typically need the input tempo TI and the selected tempo T, or their ratio, which can be sent over a tempo connection 140 as a signal, coded number or any equivalent well known from prior art. Tempo adjustment between the input audio signal and the output audio signal may occur without selection of an input audio signal with a particular tempo, hence e.g. with a fixed input audio signal, or in combination with input audio signal selection e.g. to correct for small deviations of the input tempo TI from the selected tempo T for the output audio signal o. Note that the value of the predefined deviation d for selection may be larger than for tempo adjustment. In the first case it limits the number of songs that can be chosen from the audio database, whereas in the second case it is a tolerance on the tempo adjustment accuracy.

Figure 2:
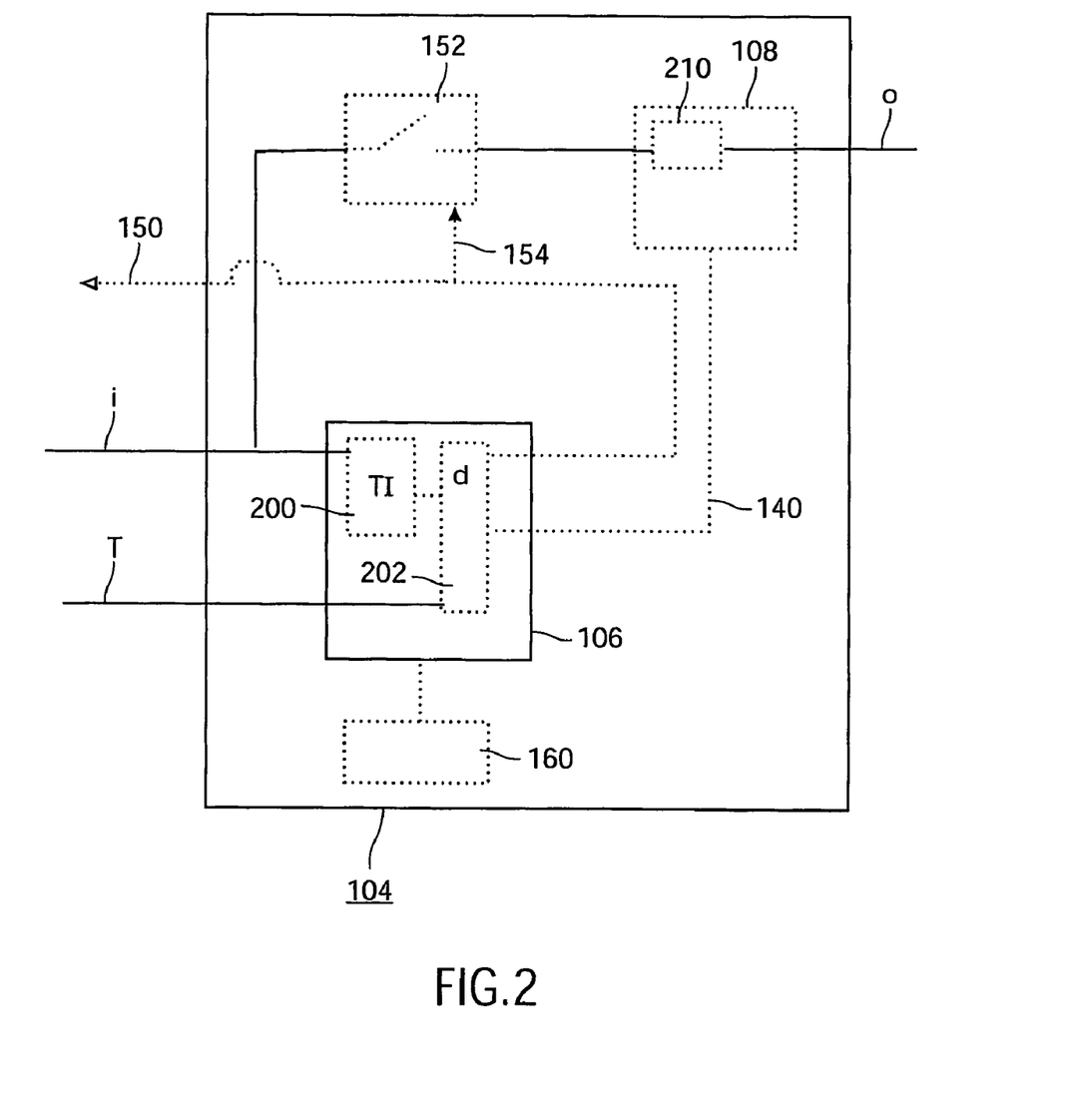
FIG. 2 schematically shows an embodiment of an audio-conditioning unit.

FIG. 2 schematically shows an embodiment of an audio-conditioning unit 104, in which the dashed components may or may not be present in different configurations. An input tempo calculation part 200 is drawn explicitly, which is arranged to apply e.g. the algorithm explained by means of FIG. 4 to obtain the input tempo TI. A tempo comparator 202 is arranged to compare the calculated input tempo TI with the selected tempo T, and to send a "next audio piece" signal over the selection means 150 if their absolute difference is outside the predefined deviation d range, or by means of another tempo heuristic. Note that in the drawn example of this embodiment the control signal of the first control connection 154 is also sent over the selection means 150 by the tempo comparator 202, but this may be implemented with a different connection. The tempo comparator 202 may also be arranged to send the input tempo TI and the selected tempo T over the tempo connection 140 in case tempo adjustment by the audio processing unit is required as a result of a decision strategy evaluation of the tempo comparator 202.

The audio-processing unit 210 may also comprise a local tempo variation unit 210, arranged to apply an alternative tempo adjustment for selected local time segments of the output audio signal. In other words, the local tempo variation unit 210 is arranged to apply between a first input audio segment and a first output audio segment, based on the first input audio segment, a first tempo adjustment with a first tempo change, and to apply between a second input audio segment and a second output audio segment, based on the second input audio segment, a second tempo adjustment with a second tempo change, whereby the first tempo change is different from the second tempo change. The adjustment can also be made by re-processing certain parts of the output audio signal after a global tempo adjustment. Especially for particular types of music, e.g. stretching single notes played on e.g. a brass instrument in relation to the tempo of the rest of the song, can give the music an even slower impression. This can be interesting during the relaxation part after training. The local tempo variation unit 210 may perform automatic analysis to detect whether particular instruments are present and in which time segments. It may also be arranged to check for tags indicating that there are notes played by particular instruments at particular times.

Figure 3:
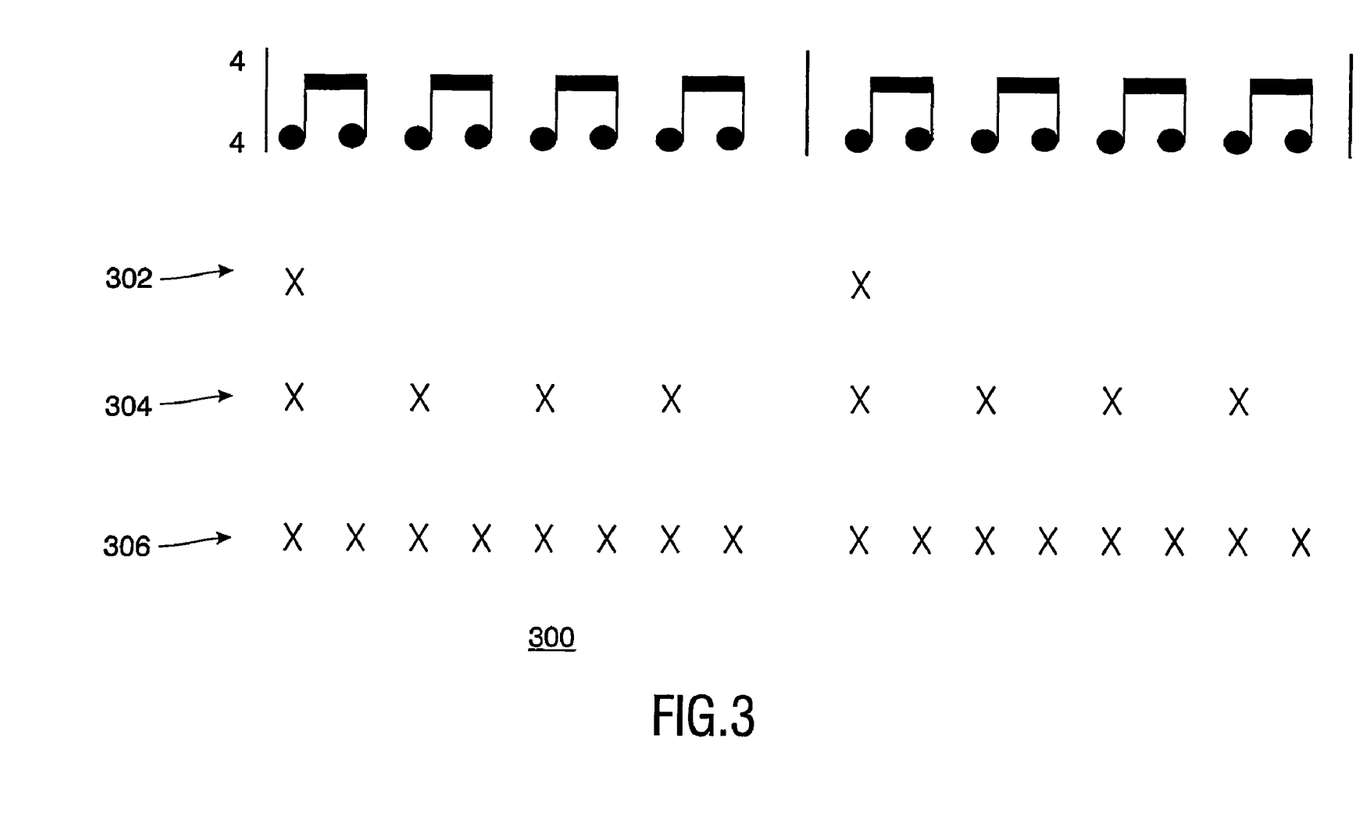
FIG. 3 introduces the nomenclature used for characterizing the meter of a piece of music.

FIG. 3 introduces the nomenclature used for characterizing the meter of a piece of music. The meter is the hierarchy of time instances of particular events that describes a particular piece of music. An event is e.g. the playing of a note or the stressing of a note. The lowest level 306 is called the tatum, and coincides with the playing of single notes. Note detection is starting point of a typical tempo calculator. The second level 304 is the level of the beat or tactus. The number of beats per minutes is a measure of tempo. It is identified by marking stress notes. Stress can be applied to a note e.g. by playing it louder or by a number of other variations such as pitch variations, temporal shifts, etc. The highest level 302 shown is the measure or bar.

Figure 4A:
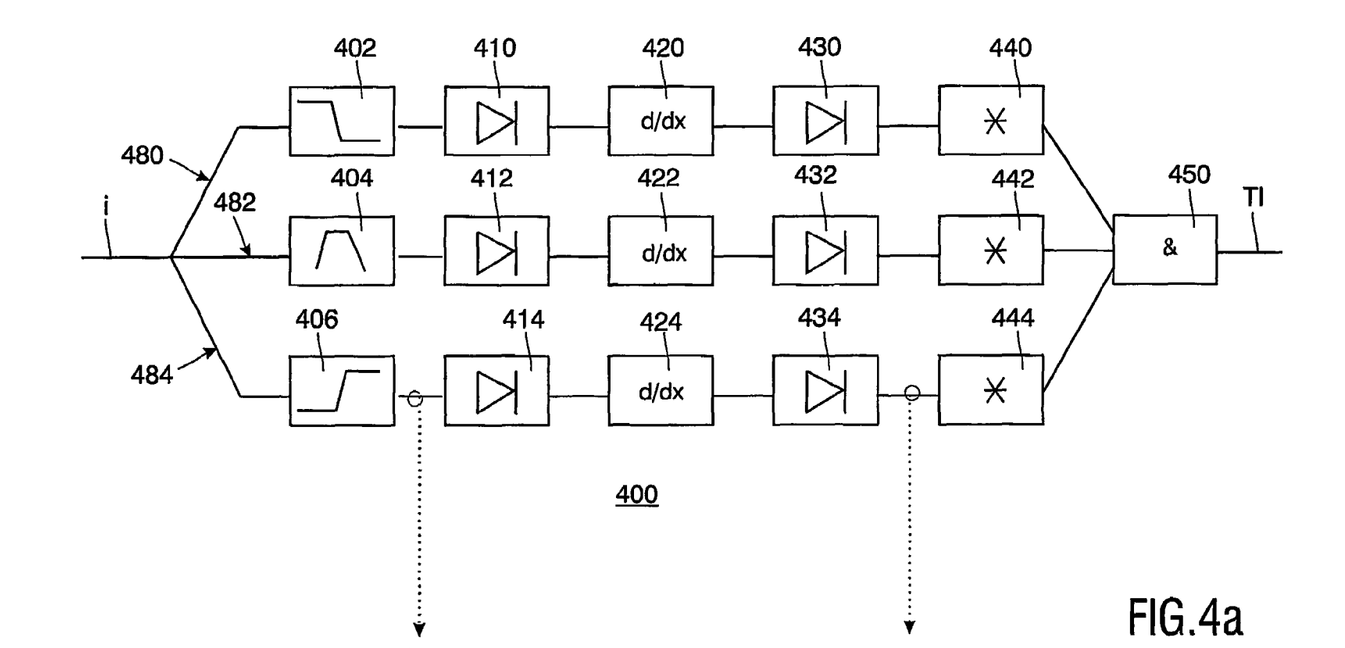
FIGS. 4*a* and 4*b* schematically shows an example embodiment of a tempo calculation unit.

FIG. 4a schematically shows an example embodiment 400 of a tempo calculation part 200. It proves favorable for accurate tempo calculation to split an audio signal in multiple frequency bands by means of filters 402, 404, 406. These filters 402, 404, 406 are also designed to assure that the calculation occurs at the time scale of the tempo and not the time scale of the pitch. The filtered signal is rectified by means of rectifiers 410, 412, 414 and the spatial difference signal is calculated by means of differentiators 420, 422, 424. Further rectifiers 430, 432, 434 are present so that only the increasing slope differences are retained. Correlators 440, 442, 444 are present to evaluate the periodicity of the rectifier difference pulses. Analysis logic combines these periodicities, leading to a most probable tatum prediction and looks for stress patterns in the tatum pattern, finally leading to the tempo. A particular variant using oscillators for analyzing the periodicity is described in "Eric D. Scheirer: Tempo and beat analysis of acoustic musical signals. Journal of the acoustic Society of America 103, no. 1, 1998, pp. 588-601.".

Figure 4B:
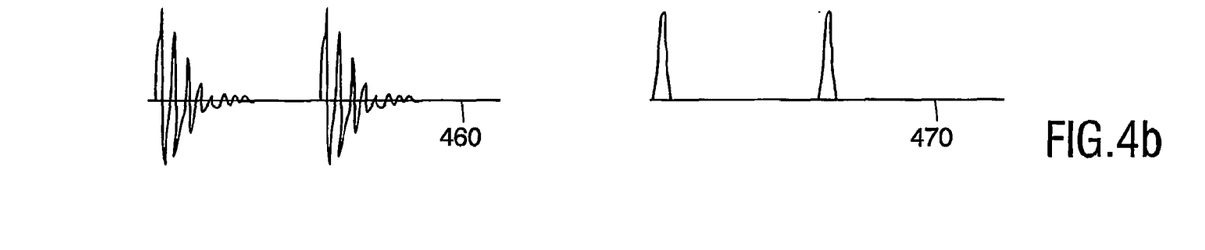

FIG. 4b schematically shows what the audio signal looks like in a third processing branch 484, namely a filtered signal 460 behind a third filter 406 and a rectified difference signal 470 behind a sixth rectifier 434.

Figure 5:
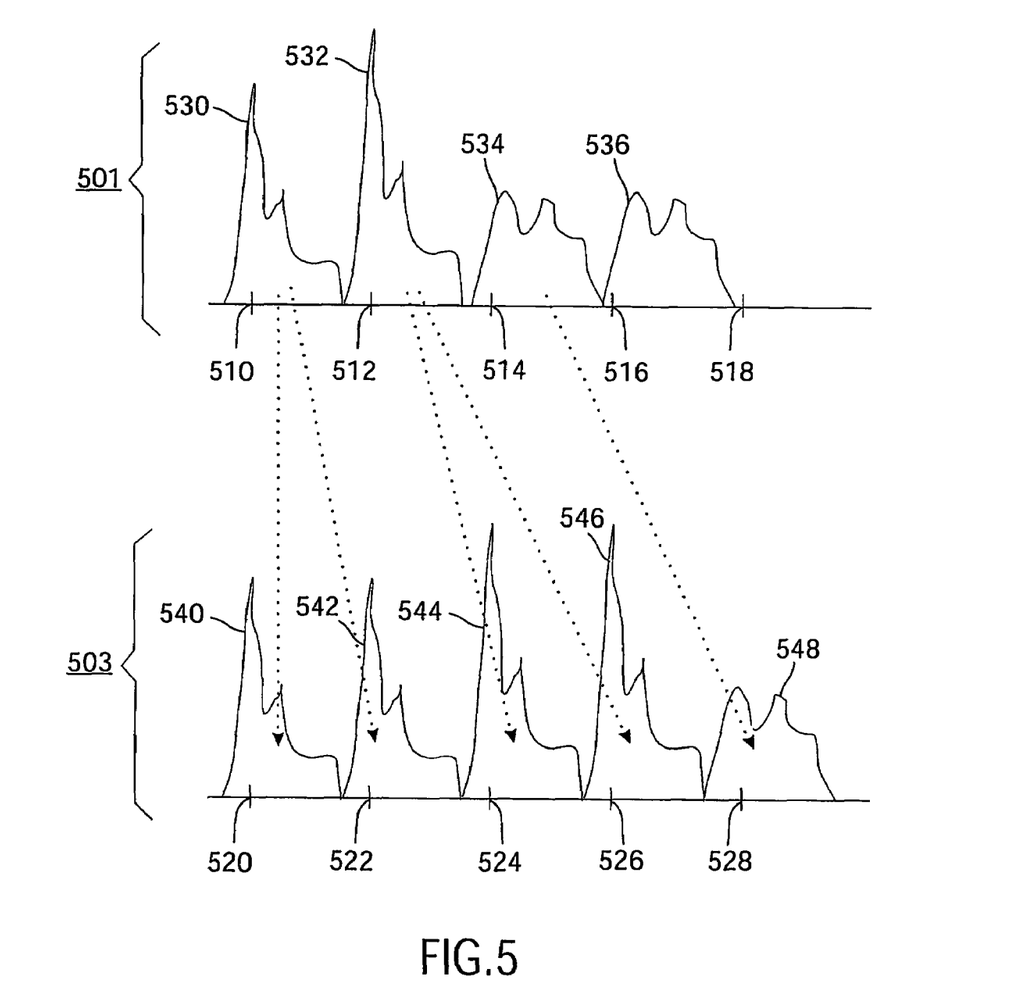
FIG. 5 schematically shows the signal processing of a particular pitch preserving tempo changing algorithm.

FIG. 5 schematically shows the signal processing of a particular pitch preserving tempo changing algorithm, in a case in which the input tempo TI is twice the selected tempo T. The fundamental idea is that audio consists of repetitive patterns, hence if similar patterns are inserted in between, a longer stretch of audio is obtained without significant alteration of the other perceptible characteristics of the audio, and in particular the pitch. Similarly, if a shorter duration audio signal is required, some of the numerous similar patterns can be dropped.

A first input segment 530 and a second input segment 532 are similar, as can be verified with a number of different similarity criteria. The output audio signal o can be constructed digitally by first setting all required samples equal to zero. The samples of the first input segment 530 at a first input time instance 510 are copied to a first output time instance 520 to obtain a first output audio segment 540. The second input segment is drawn a little larger, symbolizing that the amplitude of an envelope of the input audio signal is slowly rising. Since for a tempo halving the amplitude variation of the output audio signal should be twice as slow, the second input segment 532 is copied to a third output time instance 524 to obtain a third output audio segment 544. There is no input data for a second output time instance 522. But the output audio segment residing there should be similar to the first and the second output audio segment 540 resp. 544. Hence a second output audio segment 542 is constructed based on a weighed combination of samples from e.g. the first and second input audio segment 530 resp. 532, e.g. by means of equation 1:

$$y(k) = \frac{\sum_i w^2(k - iD + \Delta_i)x(k - iD + \Delta_i + \tau^{-1}(iD))}{\sum_i w^2(k - iD + \Delta_i)} \quad [1]$$

In equation [1], the output audio signal y(k) is synthesized at all discrete times k, by overlap, at a discrete number of synthesis time instances—enumerated by i and positioned a temporal distance D apart—of audio segments excised from the input audio signal x. It is further assumed in equation [6] that both the excised and synthesized audio segments are weighted by the same weighing function w. $\tau^{-1}$ (iD) is the analysis time instance corresponding to a synthesis time instance iD, where excision of a audio segment from the input audio signal has to occur. However, when adding an excised audio segment to a part of the output audio signal already synthesized, one has to be careful that an excised audio segment from the input audio signal resembles closely an audio segment which is expected to follow the part of the output audio signal already synthesized. Therefore a small offset $\Delta_i$ is introduced, which allows for excision of an audio segment at a slightly different discrete time than $\tau^{-1}$ (iD).

Figure 6A:
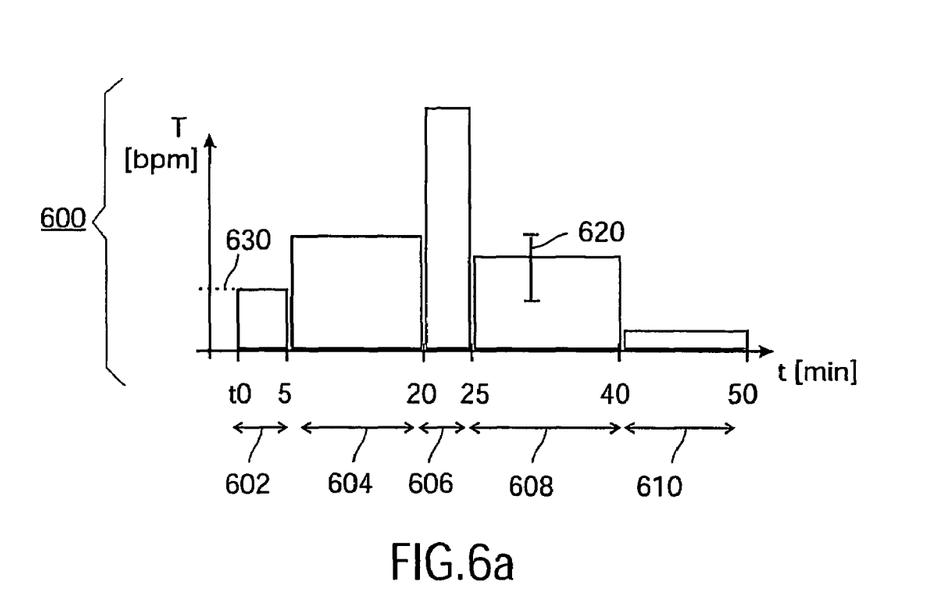
FIGS. 6*a* and 6*b* shows two example workout specifications.

FIG. 6a shows an example of a temporal workout specification 600 which can be specified by a user and stored in memory in the workout scheme specification unit 180, if required together with additional data such as e.g. the name of the user, the date etc. The workout scheme specification unit 180 is then arranged to send a tempo to the audio conditioning unit 104 at a corresponding time instance. The temporal workout specification 600 comprises a consecutive set of specified time intervals, such as a first time interval 602 for warming up, and corresponding desired selected tempos, such as a first selected tempo 630. If the audio reproduction apparatus 100 is in a mode which adapts itself to the user's performance on short time scales rather than to use a fixed temporal workout specification, a user may want to deviate at certain instances of time from the desired selected tempo for the particular time interval without the audio reproduction apparatus 100 updating the current selected tempo in the temporal workout specification 600. This is handy e.g. when he is running uphill for a short time. To achieve this, the workout scheme specification unit 180 may be arranged to allow the specification of tolerances, such as tolerance 620. The tolerances may be formulated e.g. as a lower and upper deviation from the desired selected tempo for the associated time interval and/or as a time interval during which the deviation of the current selected tempo T corresponding to e.g. the runner's pace may deviate from the desired selected tempo for the current time interval in the temporal workout specification 600 by an arbitrary amount. This is handy e.g. when the user has to discontinue running because of a red traffic light.

Figure 6B:
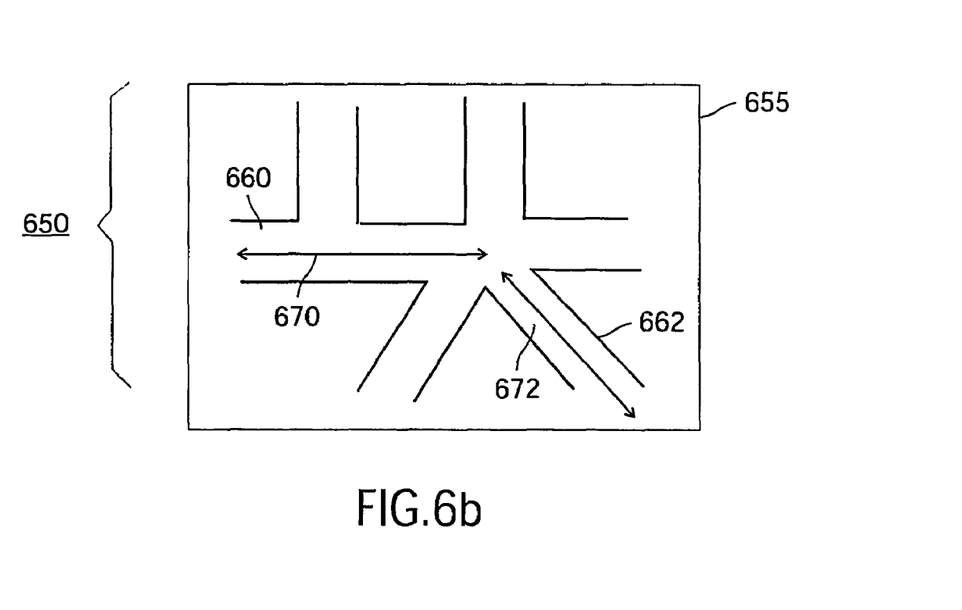

FIG. 6b shows an alternative workout specification 650, which may be advantageous in case the audio reproduction apparatus contains a display, a map of the neighborhood in memory, and localization means such as a global positioning system (GPS) unit. The user can then e.g. draw intervals such as a first spatial interval 670 on a representation of a first street 660, and a second spatial interval 672 on a representation of a second street 662, and specify corresponding tempos. As long as the user is running in the first street, the selected tempo is equal to a first value, etc.

Under computer program product should be understood any physical realization of a collection of commands enabling a processor-generic or special purpose-, after a series of loading steps to get the commands into the processor, to execute any of the characteristic functions disclosed in the present invention. In particular the computer program product may be realized as data on a carrier such as e.g. a disk or tape, data present in a memory, data traveling over a network connection-wired or wireless-, or program code on paper.

It should be noted that the above-mentioned embodiments illustrate rather than limit the invention and that those skilled in the art are able to design alternatives, without departing from the scope of the claims. Apart from combinations of elements of the invention as combined in the claims, other combinations of the elements within the scope of the invention as perceived by one skilled in the art are covered by the invention. Any combination of elements can be realized in a single dedicated element. Any reference sign between parentheses in the claim is not intended for limiting the claim. The word "comprising" does not exclude the presence of elements or aspects not listed in a claim. The word "a" or "an" preceding an element does not exclude the presence of a plurality of such elements.

The invention can be implemented by means of hardware or by means of software running on a computer, and previously stored on a data carrier or transmitted over a signal transmission system.

The invention claimed is:

1. An audio reproduction apparatus suitable for use during sports training comprising:
   an input configured to receive an input audio signal;
   a user behavior identification unit configured to derive a tempo output on a basis of a data signal;
   an audio conditioning unit which generates an output audio signal dependent on the derived tempo output from the user behavior identification unit, the audio conditioning unit including:
      a tempo calculation unit which calculates an input tempo of the input audio signal,
      an audio processing unit which constructs, based on the input audio signal, the output audio signal with an output tempo closer to the derived tempo than the input tempo, and with an output pitch substantially equal to an input pitch of the input audio signal, the audio processing unit constructing the output audio signal by:
         starting with a substantially zero value output audio signal,
         selecting audio segments of consecutive samples of the audio input signal which meet an audio segment similarity criterion,
         weighting the selected audio segments;
         adding the selected and weighted audio segments to the output audio signal at output time instances determined by a ratio between the selected tempo and the input tempo; and
   an output configured to output the output audio signal.

2. The audio reproduction apparatus as claimed in claim 1, further including:
   a physiological monitor which generates the data signal from which the tempo output is derived.

3. The audio reproduction apparatus as claimed in claim 1, wherein the audio conditioning unit further includes:
   a tempo comparator which
      compares the input tempo with the derived tempo and determines whether the input tempo is within a predefined deviation of the derived tempo and
      generates a selection signal in response to the input tempo differing from the derived tempo by more than the predefined deviation, the selection signal being used to select a different input audio signal having an input tempo closer to the derived tempo.

4. The audio reproduction apparatus as claimed in claim 3, further including:
   an audio source which supplies the input audio signal and which receives and responds to the selection signal by sending the different audio input signal.

5. The audio reproduction apparatus as claimed in claim 4, wherein the audio conditioning unit further includes:
   a memory in which a table of audio pieces contained in the audio source is stored with the input tempo which the input calculation unit calculated such that the selection signal selects the different audio piece in accordance with the derived tempo.

6. The audio reproduction apparatus as claimed in claim 1, wherein the audio processing unit includes:
   a local tempo variation unit which applies a first tempo adjustment with a first tempo change between a first input audio segment and a first output audio segment and a second tempo adjustment with a second tempo change between a second input audio segment and a second output audio segment, the first tempo change being different from the second tempo change.

7. An audio reproduction apparatus for use during sports training, the audio reproduction apparatus comprising:
- a tempo unit which generates a selected output tempo;
- an audio conditioning unit which generates an output audio signal, the audio conditioning unit including:
  - a tempo calculation unit which calculates an input tempo of an input audio signal,
  - a tempo comparing unit which compares the calculated input audio tempo and the selected output tempo, in response to the input audio tempo differing from the selected output tempo by more than a preselected threshold, the tempo comparing unit generates an output signal requesting a different audio input signal,
  - an audio processing unit which modifies the input audio signal to have a tempo closer to the selected output tempo and with the modified input signal having a pitch substantially equal to a pitch of the input audio signal, the audio processing unit:
    - dividing the input audio signal into audio segments,
    - adjusting a temporal interval between adjacent audio segments to modify the input audio segment to assume a tempo closer to the selected tempo,
    - repeating at least some of the audio segments modifying the tempo of the input audio signal to be closer to the selected output tempo; and,
- an audio output by which the modified input audio signal is output as an output audio signal for a sound production means.

8. The audio reproduction apparatus as claimed in claim 7, further including:
- a physiological monitor which generates a signal indicative of exercise level; and
- a tempo derivation unit which generates the selected output tempo based on the physiological monitor output signal.

9. The audio reproduction apparatus as claimed in claim 7, further including:
- an audio source which contains a plurality of audio pieces, the audio source supplying one of the audio pieces as the input audio signal and in response to the tempo comparator unit determining that the input tempo and the selected tempo differ by greater than the preselected threshold, supplies a different audio piece as the audio input.

10. The audio reproduction apparatus as claimed in claim 9, further including:
- a memory which stores a table of the audio pieces contained in the audio source and the calculated tempo of each audio piece.

11. The audio reproduction apparatus as claimed in claim 7, wherein the audio processing unit moves the audio segments further apart leaving gaps between audio signals and fills the gaps by reproducing and adding at least some of the audio segments in the gaps.

12. The audio reproduction apparatus as claimed in claim 11, wherein the audio processing unit adjusts the added segments in accordance with a size of the gap into which it is filling and in accordance with adjacent audio segments.

13. The audio reproduction apparatus as claimed in claim 11, further including:
- a local tempo variation unit which analyzes the input signal to identify whether at least preselected instruments are present in the input signal and time segments of the input signal in which each identified instrument is present.

14. The audio reproduction apparatus as claimed in claim 13, wherein the tempo calculation unit determines a tempo for each identified preselected instrument and the audio processing unit modifies the tempo for each identified preselected instrument.

15. The audio reproduction apparatus as claimed in claim 13, wherein the tempo calculation unit includes:
- a plurality of frequency filters which split the input audio signal into a plurality of paths;
- a unit which calculates a spatial difference sequence for each path;
- a circuit which evaluates each path to determine a tatum prediction, the input tempo being calculated from the tatum prediction.

16. The audio reproduction apparatus as claimed in claim 13, wherein the tempo calculation unit includes a plurality of parallel signal paths, each path including:
- a frequency filter to limit each path to a selected frequency band;
- a first rectifier which rectifies an output of the filter;
- a differentiation circuit which differentiates an output of the first rectifier to generate a spatial difference signal;
- a second rectifier which rectifies an output of the differentiator circuit such that only slope differences are retained;
- correlation units which evaluate a periodicity of an output of the rectifier; and
- wherein the plurality of paths are connected with an analysis logic unit which combines the periodicities, determines a tatum pattern, looks for stress patterns in the tatum pattern, and calculates the tempo.

17. The audio reproduction apparatus as claimed in claim 7, wherein the output audio signal y(x) is defined by:

$$y(k) = \frac{\sum_i w^2(k - iD + \Delta_i) x(k - iD + \Delta_i + \tau^{-1}(iD))}{\sum_i w^2(k - iD + \Delta_i)}$$

wherein the output audio signal y(k) is synthesized at discrete times k by overlap at a discrete number of synthesis time instances, enumerated by y and positioned a temporal distance D apart, of audio segments excised from the input audio signal x, the excised audio segments and synthesized audio segments being weighted by a weighting factor w, wherein $\tau^1$ (iD) is an analysis time instance corresponding to a synthesis time instance iD, where excision of the audio segment from the input audio signal occurs, and wherein the $\Delta^1$ is an offset which allows for the excision of the audio segment at a different discrete time than $\tau^1$(iD).

18. The audio reproduction apparatus as claimed in claim 17, further including:
- a physiological monitor which generates a signal indicative of a patient's physical activity level; and,
- a unit which converts the physiological monitor signal into the selected tempo and overrides the tempo specified in the workout specification memory such that the workout specification adapts for temporary increases in physical activity and for temporary reductions or terminations of physical activity.

19. The audio reproduction apparatus as claimed in claim 7, further including:
- a temporal workout specification memory which stores a series of time intervals specified by a user and the selected tempo for each specified time interval such that the tempo of the output audio signal varies with the specified time intervals.

20. The audio reproduction apparatus as claimed in claim 7, further including:
a memory for storing a map;
a display for displaying the map;
an input by which a user identifies legs of a workout route on the map and an exercise level or tempo for each identified leg;
a localizing means such as a global positioning system for identifying the user's location along the exercise route, the tempo selection unit selecting the tempo in accordance with the identified user's location and the exercise level or tempo for a corresponding leg stored in the map memory.

* * * * *